(12) United States Patent
Old

(10) Patent No.: US 8,202,855 B2
(45) Date of Patent: Jun. 19, 2012

(54) SUBSTITUTED BETA-LACTAMS

(75) Inventor: David W. Old, Irvine, CA (US)

(73) Assignee: Allergan, Inc, Irvine, CA (US)

( * ) Notice: Subject to any disclaimer, the term of this patent is extended or adjusted under 35 U.S.C. 154(b) by 359 days.

(21) Appl. No.: 12/395,813

(22) Filed: Mar. 2, 2009

(65) Prior Publication Data

US 2009/0227557 A1    Sep. 10, 2009

Related U.S. Application Data

(60) Provisional application No. 61/033,601, filed on Mar. 4, 2008.

(51) Int. Cl.
| C07D 205/08 | (2006.01) |
| C07D 409/06 | (2006.01) |
| A61P 17/14 | (2006.01) |
| A61P 27/06 | (2006.01) |
| A61P 1/00 | (2006.01) |
| C07D 401/06 | (2006.01) |
| C07D 407/06 | (2006.01) |

(52) U.S. Cl. .................... 514/210.02; 540/200
(58) Field of Classification Search ............ 540/200; 514/210.02
See application file for complete search history.

(56) References Cited

U.S. PATENT DOCUMENTS

| 4,166,452 A | 9/1979 | Generales |
| 4,174,316 A | 11/1979 | Christensen |
| 4,256,108 A | 3/1981 | Theeuwes |
| 4,265,874 A | 5/1981 | Bousen |
| 6,437,146 B1 | 8/2002 | Hattori |
| 6,710,072 B2 | 3/2004 | Burk |
| 6,747,054 B2 | 6/2004 | Cameron |
| 7,674,786 B2 * | 3/2010 | Old et al. ............ 514/210.02 |
| 7,772,392 B2 * | 8/2010 | Old et al. ............ 540/200 |
| 2003/0120079 A1 | 6/2003 | Elworthy |
| 2003/0207925 A1 | 11/2003 | Cameron |
| 2009/0186866 A1 * | 7/2009 | Old et al. ............ 514/210.02 |
| 2009/0318404 A1 * | 12/2009 | Old ............ 514/210.02 |

FOREIGN PATENT DOCUMENTS

WO    WO 2006/121708    11/2006

OTHER PUBLICATIONS

Remington's Pharmaceutical Sciences, Mack Publishing Company, Easton, Pa., 16th Edition, 1980.
Yamada, Tchru; et al.: The Asymmetric Addition of the Sn(II) Enolates of Thicesters to α-Iminoesters. A Convenient Synthesis of Optically Active Cis-Substituted β-Lactams. Chemistry Letters, (2), 293-6; 1987.

* cited by examiner

Primary Examiner — Mark Berch
(74) Attorney, Agent, or Firm — Kevin J. Forrestal; John E. Wurst; Doina G. Ene

(57) ABSTRACT

Disclosed herein is a compound comprising a formula

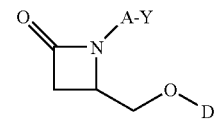

or a pharmaceutically acceptable salt or a prodrug or a metabolite thereof;
Y is

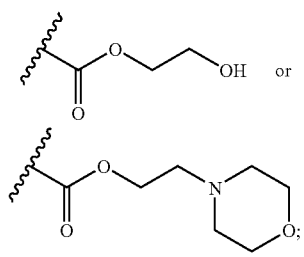

A is $-(CH_2)_6-$, cis $-CH_2CH{=}CH-(CH_2)_3-$, or $-CH_2C{\equiv}C-(CH_2)_3-$, wherein 1 or 2 carbon atoms may be substituted with S or O; or A is $-(CH_2)_m-Ar-(CH_2)_o-$ wherein Ar is interarylene or heterointerarylene, the sum of m and o is from 1 to 4, and wherein one $CH_2$ may be substituted with S or O; and
D is aryl or heteroaryl.
Methods of use are also disclosed.

7 Claims, No Drawings

SUBSTITUTED BETA-LACTAMS

RELATED APPLICATION

This application claims the benefit of U.S. Provisional Application Ser. No. 61/033,601, filed Mar. 4, 2008, the disclosure of which is hereby incorporated in its entirety herein by reference.

BACKGROUND OF THE INVENTION

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

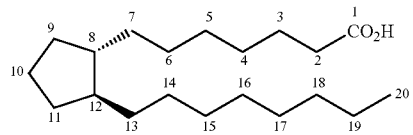

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY OF THE INVENTION

Disclosed herein are compounds useful in treating glaucoma, inflammatory bowel disease, the stimulation of hair growth, and the stimulation of the conversion of vellus hair to terminal hair. The compounds themselves are disclosed below.

DESCRIPTION OF THE INVENTION

Disclosed herein is a compound comprising

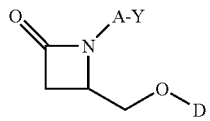

or a pharmaceutically acceptable salt or a prodrug or a metabolite thereof;
Y is

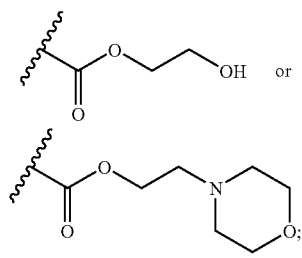

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and D is aryl or heteroaryl.

In relation to the identity of A disclosed in the chemical structures presented herein, A is —(CH$_2$)$_6$—, cis —CH$_2$CH=CH—(CH$_2$)$_3$—, or —CH$_2$C≡C—(CH$_2$)$_3$—, where 1 or 2 carbon atoms may be substituted with S or O; or A is —(CH$_2$)$_n$—Ar—(CH$_2$)$_o$— wherein Ar is interarylene or heterointerarylene, the sum of m and o is from 1 to 4, and wherein one CH$_2$ may be substituted with S or O.

While not intending to be limiting, A may be —(CH$_2$)$_6$—, cis —CH$_2$CH=CH—(CH$_2$)$_3$—, or —CH$_2$C≡C—(CH$_2$)$_3$—.

Alternatively, A may be a group which is related to one of these three moieties in that any carbon is substituted with S and/or O. For example, while not intending to limit the scope of the invention in any way, A may be an S substituted moiety such as one of the following or the like.

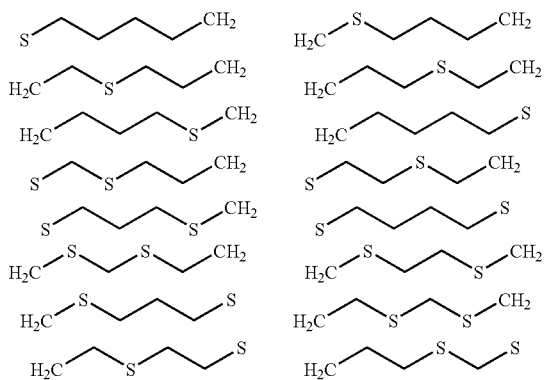

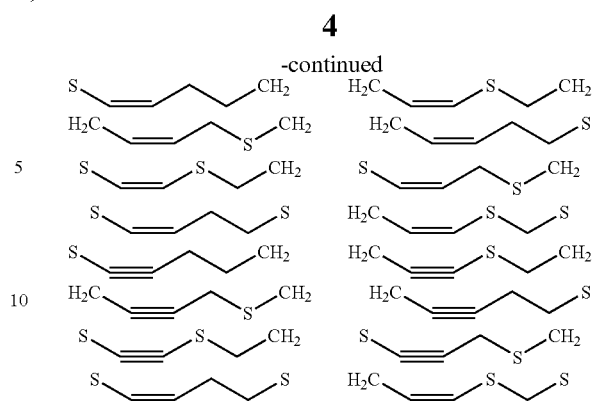

Alternatively, while not intending to limit the scope of the invention in any way, A may be an O substituted moiety such as one of the following or the like.

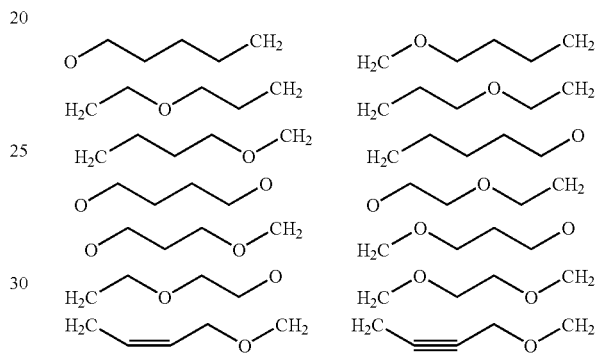

Alternatively, while not intending to limit the scope of the invention in any way, A may have both an O and an S substituted into the chain, such as one of the following or the like.

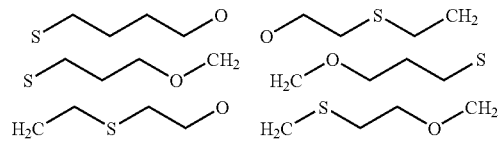

Alternatively, while not intending to limit the scope of the invention in any way, in certain embodiments A is —(CH$_2$)$_n$—Ar—(CH$_2$)$_o$— wherein Ar is interarylene or heterointerarylene, the sum of m and o is from 1 to 4, and wherein one CH$_2$ may be substituted with S or O. In other words, while not intending to limit the scope of the invention in any way, in one embodiment A comprises from 1 to 4 CH$_2$ moieties and Ar, e.g. —CH$_2$—Ar—, —(CH$_2$)$_2$—Ar—, —CH$_2$—Ar—CH$_2$—, —CH$_2$Ar—(CH$_2$)$_2$—, —(CH$_2$)$_2$—Ar—(CH$_2$)$_2$—, and the like; or A comprises O, from 0 to 3 CH$_2$ moieties, and Ar, e.g., —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or A comprises S, from 0 to 3 CH$_2$ moieties, and Ar, e.g., —S—Ar—, Ar—CH$_2$—S—, —S—Ar—(CH$_2$)$_2$—, —S—CH$_2$—Ar—, —S—CH$_2$—Ar—(CH$_2$)$_2$, —(CH$_2$)$_2$—S—Ar, and the like.

In another embodiment, the sum of n and o is from 2 to 4 wherein one CH$_2$ may be substituted with S or O.

In another embodiment, the sum of n and o is 3 wherein one CH$_2$ may be substituted with S or O.

In another embodiment, the sum of n and o is 2 wherein one CH$_2$ may be substituted with S or O.

In another embodiment, the sum of n and o is 4 wherein one CH$_2$ may be substituted with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. While not intending to limit scope of the invention in any way, substituents may have 4 or less heavy atoms, or in other words, non hydrogen atoms. Any number of hydrogen atoms required for a particular substituent will also be included. Thus, the substituent may be hydrocarbyl having up to 4 carbon atoms, including alkyl up
  to C$_4$, alkenyl, alkynyl, and the like;
hydrocarbyloxy up to C$_3$;
CF$_3$;
halo, such as F, Cl, or Br;
hydroxyl;
NH$_2$ and alkylamine functional groups up to C$_3$;
other N or S containing substituents;
and the like.

In one embodiment A is —(CH$_2$)$_m$—Ar—(CH$_2$)$_o$— wherein Ar is interphenylene, the sum of m and o is from 1 to 3, and wherein one CH$_2$ may be substituted with S or O.

In another embodiment A is —CH$_2$—Ar—OCH$_2$—. In another embodiment A is —CH$_2$—Ar—OCH$_2$— and Ar is interphenylene. In another embodiment, Ar is attached at the 1 and 3 positions, otherwise known as m-interphenylene, such as when A has the structure shown below.

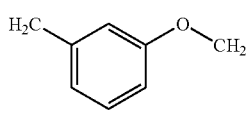

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph- wherein one CH$_2$ may be substituted with S or O.

In another embodiment A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_2$-Ph-.

In other embodiments, A has one of the following structures, where Y is attached to the aromatic or heteroaromatic ring.

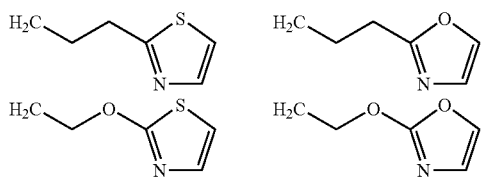

-continued

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$O(CH$_2$)$_4$.
In another embodiment A is —CH$_2$S(CH$_2$)$_4$.
In another embodiment A is —(CH$_2$)$_6$—.
In another embodiment A is cis —CH$_2$CH═CH—(CH$_2$)$_3$—.
In another embodiment A is —CH$_2$C≡C—(CH$_2$)$_3$—.
In another embodiment A is —S(CH$_2$)$_3$S(CH$_2$)$_2$—.
In another embodiment A is —(CH$_2$)$_4$OCH$_2$—.
In another embodiment A is cis —CH$_2$CH═CH—CH$_2$OCH$_2$—.
In another embodiment A is —CH$_2$CH≡CH—CH$_2$OCH$_2$—.
In another embodiment A is —(CH$_2$)$_2$S(CH$_2$)$_3$—.
In another embodiment A is —CH$_2$-Ph-OCH$_2$—, wherein Ph is interphenylene.
In another embodiment A is —CH$_2$-mPh-OCH$_2$—, wherein mPh is m-interphenylene,.
In another embodiment A is —CH$_2$—O—(CH$_2$)$_4$—.
In another embodiment A is —CH$_2$—O—CH$_2$—Ar—, wherein Ar is 2,5-interthienylene.
In another embodiment A is —CH$_2$—O—CH$_2$—Ar—, wherein Ar is 2,5-interfurylene.

D is aryl or heteroaryl.

Aryl is an unsubstituted or substituted aromatic ring or ring system such as phenyl, naphthyl, biphenyl, and the like.

Heteroaryl is aryl having one or more N, O, or S atoms in the ring, i.e. a ring carbon is substituted by N, O, or S. While not intending to be limiting, examples of heteroaryl include unsubstituted or substituted thienyl, pyridinyl, furyl, benzothienyl, benzofuryl, imidizololyl, indolyl, and the like.

The substituents of aryl or heteroaryl may have up to 12 non-hydrogen atoms each and as many hydrogen atoms as necessary. Thus, while not intending to limit the scope of the invention in any way, the substituents may be:
hydrocarbyl, such as alkyl, alkenyl, alkynyl, and the like, including linear, branched or cyclic hydrocarbyl, and combinations thereof;
hydrocarbyloxy, meaning O-hydrocarbyl such as OCH$_3$, OCH$_2$CH$_3$, O-cyclohexyl, etc, up to 11 carbon atoms;
hydroxyhydrocarbyl, meaning hydrocarbyl-OH such as CH$_2$OH, C(CH$_3$)$_2$OH, etc, up to 11 carbon atoms;
nitrogen substituents such as NO$_2$, CN, and the like, including amino, such as NH$_2$, NH(CH$_2$CH$_3$OH), NHCH$_3$, and the like up to 11 carbon atoms;
carbonyl substituents, such as CO$_2$H, ester, amide, and the like;
halogen, such as chloro, fluoro, bromo, and the like
fluorocarbyl, such as CF$_3$, CF$_2$CF$_3$, etc.;
phosphorous substituents, such as PO$_3^{2-}$, and the like;
sulfur substituents, including S-hydrocarbyl, SH, SO$_3$H, SO$_2$-hydrocarbyl, SO$_3$-hydrocarbyl, and the like.

In certain embodiments, the number of non-hydrogen atoms is 6 or less in a substituent. In other embodiments, the number of non-hydrogen atoms is 3 or less in a substituent. In other embodiments, the number of non-hydrogen atoms on a substituent is 1.

In certain embodiments, the substituents contain only hydrogen, carbon, oxygen, halogen, nitrogen, and sulfur. In other embodiments, the substituents contain only hydrogen, carbon, oxygen, and halogen.

Unless otherwise indicated, references to aryl, heteroaryl, phenyl, thienyl, benzothienyl, and the like are intended to mean both the substituted and the unsubstituted moiety.

Thus, compounds wherein D is any of the above classes or species of aryl or heteroaryl are contemplated herein.

Further, while not intending to limit the scope of the invention in any way, in one embodiment D is phenyl. In another embodiment D is chlorophenyl, meaning phenyl with one or more chloro substituents. In another embodiment D is 3,5-dichlorophenyl. In another embodiment D is unsubstituted phenyl.

In other useful compounds, D is one of the structures shown below, with the corresponding name of the structures shown.

(1-hydroxyhexyl)phenyl (1-hydroxy-2,2-dimethylpropyl)phenyl (1-hydroxy-2-methylpropyl)phenyl (hydroxymethyl)phenyl

[(1-propylcyclobutyl)hydroxymethyl]phenyl t-butylphenyl (cyclohexylhydroxymethyl)phenyl (cyclohexylmethyl)phenyl indanyl indanolyl indanonyl (1-hydroxycyclobutyl)phenyl (2-methyl-3-hydroxypropyl)phenyl (1-hydroxy-2-phenylethyl)phenyl Attachment to the remaining part of the molecule, i.e. the oxygen of the —OCH$_2$-connected to the β-lactam occurs at the phenyl ring at any position. For example, the compounds shown below, or pharmaceutically acceptable salts or prodrugs thereof, are contemplated.

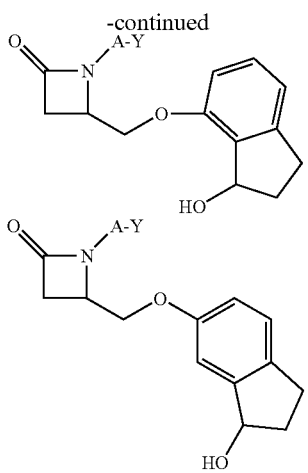

In one embodiment D is (1-hydroxyhexyl)phenyl.

In another embodiment D is (1-hydroxy-2,2-dimethylpropyl)phenyl.

In another embodiment D is (1-hydroxy-2-methylpropyl)phenyl.

In another embodiment D is (hydroxymethyl)phenyl.

In another embodiment D is [(1-propylcyclobutyl)hydroxymethyl]phenyl.

In another embodiment D is t-butylphenyl.

In another embodiment D is (cyclohexylhydroxymethyl)phenyl.

In another embodiment D is (cyclohexylmethyl)phenyl.

In another embodiment D is indanyl.

In another embodiment D is indanolyl.

In another embodiment D is indanonyl.

In another embodiment D is (1-hydroxycyclobutyl)phenyl.

In another embodiment D is (2-methyl-3-hydroxypropyl)phenyl.

In another embodiment D is (1-hydroxy-2-phenylethyl)phenyl.

In one embodiment A is —$(CH_2)_6$—, and D is (1-hydroxyhexyl)phenyl.

In another embodiment A is cis —$CH_2CH=CH$—$(CH_2)_3$—, and D is (1-hydroxyhexyl)phenyl.

In another embodiment A is —$CH_2C\equiv C$—$(CH_2)_3$—, and D is (1-hydroxyhexyl)phenyl.

In another embodiment A is —$S(CH_2)_3S(CH_2)_2$—, and D is (1-hydroxyhexyl)phenyl.

In another embodiment A is —$(CH_2)_4OCH_2$—, and D is (1-hydroxyhexyl)phenyl.

In another embodiment A is cis —$CH_2CH=CH$—$CH_2OCH_2$—, and D is (1-hydroxyhexyl)phenyl.

In another embodiment A is —$CH_2CH=CH$—$CH_2OCH_2$—, and D is (1-hydroxyhexyl)phenyl.

In another embodiment A is —$(CH_2)_2S(CH_2)_3$—, and D is (1-hydroxyhexyl)phenyl.

In another embodiment A is —$CH_2$-Ph-$OCH_2$—, wherein Ph is interphenylene, and D is (1-hydroxyhexyl)phenyl.

In another embodiment A is —$CH_2$-mPh-$OCH_2$—, wherein mPh is m-interphenylene, and D is (1-hydroxyhexyl)phenyl.

In another embodiment A is —$CH_2$—O—$(CH_2)_4$—, and D is (1-hydroxyhexyl)phenyl.

In another embodiment A is —$CH_2$—O—$CH_2$—Ar—, wherein Ar is 2,5-interthienylene, and D is (1-hydroxyhexyl)phenyl.

In another embodiment A is —$CH_2$—O—$CH_2$—Ar—, wherein Ar is 2,5-interfurylene, and D is (1-hydroxyhexyl)phenyl.

In one embodiment A is —$(CH_2)_6$—, and D is (1-hydroxy-2,2-dimethylpropyl)phenyl.

In another embodiment A is cis —$CH_2CH=CH$—$(CH_2)_3$—, and D is (1-hydroxy-2,2-dimethylpropyl)phenyl.

In another embodiment A is —$CH_2C\equiv C$—$(CH_2)_3$—, and D is (1-hydroxy-2,2-dimethylpropyl)phenyl.

In another embodiment A is —$S(CH_2)_3S(CH_2)_2$—, and D is (1-hydroxy-2,2-dimethylpropyl)phenyl.

In another embodiment A is —$(CH_2)_4OCH_2$—, and D is (1-hydroxy-2,2-dimethylpropyl)phenyl.

In another embodiment A is cis —$CH_2CH=CH$—$CH_2OCH_2$—, and D is (1-hydroxy-2,2-dimethylpropyl)phenyl.

In another embodiment A is —$CH_2CH=CH$—$CH_2OCH_2$—, and D is (1-hydroxy-2,2-dimethylpropyl)phenyl.

In another embodiment A is —$(CH_2)_2S(CH_2)_3$—, and D is (1-hydroxy-2,2-dimethylpropyl)phenyl.

In another embodiment A is —$CH_2$-Ph-$OCH_2$—, wherein Ph is interphenylene, and D is (1-hydroxy-2,2-dimethylpropyl)phenyl.

In another embodiment A is —$CH_2$-mPh-$OCH_2$—, wherein mPh is m-interphenylene, and D is (1-hydroxy-2,2-dimethylpropyl)phenyl.

In another embodiment A is —$CH_2$—O—$(CH_2)_4$—, and D is (1-hydroxy-2,2-dimethylpropyl)phenyl.

In another embodiment A is —$CH_2$—O—$CH_2$—Ar—, wherein Ar is 2,5-interthienylene, and D is (1-hydroxy-2,2-dimethylpropyl)phenyl.

In another embodiment A is —$CH_2$—O—$CH_2$—Ar—, wherein Ar is 2,5-interfurylene, and D is (1-hydroxy-2,2-dimethylpropyl)phenyl.

In one embodiment A is —$(CH_2)_6$—, and D is (1-hydroxy-2-methylpropyl)phenyl.

In another embodiment A is cis —$CH_2CH=CH$—$(CH_2)_3$—, and D is (1-hydroxy-2-methylpropyl)phenyl.

In another embodiment A is —$CH_2C\equiv C$—$(CH_2)_3$—, and D is (1-hydroxy-2-methylpropyl)phenyl.

In another embodiment A is —$S(CH_2)_3S(CH_2)_2$—, and D is (1-hydroxy-2-methylpropyl)phenyl.

In another embodiment A is —$(CH_2)_4OCH_2$—, and D is (1-hydroxy-2-methylpropyl)phenyl.

In another embodiment A is cis —$CH_2CH=CH$—$CH_2OCH_2$—, and D is (1-hydroxy-2-methylpropyl)phenyl.

In another embodiment A is —$CH_2CH=CH$—$CH_2OCH_2$—, and D is (1-hydroxy-2-methylpropyl)phenyl.

In another embodiment A is —$(CH_2)_2S(CH_2)_3$—, and D is (1-hydroxy-2-methylpropyl)phenyl.

In another embodiment A is —$CH_2$-Ph-$OCH_2$—, wherein Ph is interphenylene, and D is (1-hydroxy-2-methylpropyl)phenyl.

In another embodiment A is —$CH_2$-mPh-$OCH_2$—, wherein mPh is m-interphenylene, and D is (1-hydroxy-2-methylpropyl)phenyl.

In another embodiment A is —$CH_2$—O—$(CH_2)_4$—, and D is (1-hydroxy-2-methylpropyl)phenyl.

In another embodiment A is —$CH_2$—O—$CH_2$—Ar—, wherein Ar is 2,5-interthienylene, and D is (1-hydroxy-2-methylpropyl)phenyl.

In another embodiment A is —$CH_2$—O—$CH_2$—Ar—, wherein Ar is 2,5-interfurylene, and D is (1-hydroxy-2-methylpropyl)phenyl.

In one embodiment A is —$(CH_2)_6$—, and D is (hydroxymethyl)phenyl.

In another embodiment A is cis —CH$_2$CH=CH—(CH$_2$)$_3$—, and D is (hydroxymethyl)phenyl.

In another embodiment A is —CH$_2$C≡C—(CH$_2$)$_3$—, and D is (hydroxymethyl)phenyl.

In another embodiment A is —S(CH$_2$)$_3$S(CH$_2$)$_2$—, and D is (hydroxymethyl)phenyl.

In another embodiment A is —(CH$_2$)$_4$OCH$_2$—, and D is (hydroxymethyl)phenyl.

In another embodiment A is cis —CH$_2$CH=CH—CH$_2$OCH$_2$—, and D is (hydroxymethyl)phenyl.

In another embodiment A is —CH$_2$CH≡CH—CH$_2$OCH$_2$—, and D is (hydroxymethyl)phenyl.

In another embodiment A is —(CH$_2$)$_2$S(CH$_2$)$_3$—, and D is (hydroxymethyl)phenyl.

In another embodiment A is —CH$_2$-Ph-OCH$_2$—, wherein Ph is interphenylene, and D is (hydroxymethyl)phenyl.

In another embodiment A is —CH$_2$-mPh-OCH$_2$—, wherein mPh is m-interphenylene, and D is (hydroxymethyl)phenyl.

In another embodiment A is —CH$_2$—O—(CH$_2$)$_4$—, and D is (hydroxymethyl)phenyl.

In another embodiment A is —CH$_2$—O—CH$_2$—Ar—, wherein Ar is 2,5-interthienylene, and D is (hydroxymethyl)phenyl.

In another embodiment A is —CH$_2$—O—CH$_2$—Ar—, wherein Ar is 2,5-interfurylene, and D is (hydroxymethyl)phenyl.

In one embodiment A is —(CH$_2$)$_6$—, and D is [(1-propylcyclobutyl)hydroxymethyl]phenyl.

In another embodiment A is cis —CH$_2$CH=CH—(CH$_2$)$_3$—, and D is [(1-propylcyclobutyl)hydroxymethyl]phenyl.

In another embodiment A is —CH$_2$C≡C—(CH$_2$)$_3$—, and D is [(1-propylcyclobutyl)hydroxymethyl]phenyl.

In another embodiment A is —S(CH$_2$)$_3$S(CH$_2$)$_2$—, and D is [(1-propylcyclobutyl)hydroxymethyl]phenyl.

In another embodiment A is —(CH$_2$)$_4$OCH$_2$—, and D is [(1-propylcyclobutyl)hydroxymethyl]phenyl.

In another embodiment A is cis —CH$_2$CH=CH—CH$_2$OCH$_2$—, and D is [(1-propylcyclobutyl)hydroxymethyl]phenyl.

In another embodiment A is —CH$_2$CH≡CH—CH$_2$OCH$_2$—, and D is [(1-propylcyclobutyl)hydroxymethyl]phenyl.

In another embodiment A is —(CH$_2$)$_2$S(CH$_2$)$_3$—, and D is [(1-propylcyclobutyl)hydroxymethyl]phenyl.

In another embodiment A is —CH$_2$-Ph-OCH$_2$—, wherein Ph is interphenylene, and D is [(1-propylcyclobutyl)hydroxymethyl]phenyl.

In another embodiment A is —CH$_2$-mPh-OCH$_2$—, wherein mPh is m-interphenylene, and D is [(1-propylcyclobutyl)hydroxymethyl]phenyl.

In another embodiment A is —CH$_2$—O—(CH$_2$)$_4$—, and D is [(1-propylcyclobutyl)hydroxymethyl]phenyl.

In another embodiment A is —CH$_2$≦O—CH$_2$—Ar—, wherein Ar is 2,5-interthienylene, and D is [(1-propylcyclobutyl)hydroxymethyl]phenyl.

In another embodiment A is —CH$_2$—O—CH$_2$—Ar—, wherein Ar is 2,5-interfurylene, and D is [(1-propylcyclobutyl)hydroxymethyl]phenyl.

In one embodiment A is —(CH$_2$)$_6$—, and D is t-butylphenyl.

In another embodiment A is cis —CH$_2$CH=CH—(CH$_2$)$_3$—, and D is t-butylphenyl.

In another embodiment A is —CH$_2$C≡C—(CH$_2$)$_3$—, and D is t-butylphenyl.

In another embodiment A is —S(CH$_2$)$_3$S(CH$_2$)$_2$—, and D is t-butylphenyl.

In another embodiment A is —(CH$_2$)$_4$OCH$_2$—, and D is t-butylphenyl.

In another embodiment A is cis —CH$_2$CH=CH—CH$_2$OCH$_2$—, and D is t-butylphenyl.

In another embodiment A is —CH$_2$CH≡CH—CH$_2$OCH$_2$—, and D is t-butylphenyl.

In another embodiment A is —(CH$_2$)$_2$S(CH$_2$)$_3$—, and D is t-butylphenyl.

In another embodiment A is —CH$_2$-Ph-OCH$_2$—, wherein Ph is interphenylene, and D is t-butylphenyl.

In another embodiment A is —CH$_2$-mPh-OCH$_2$—, wherein mPh is m-interphenylene, and D is t-butylphenyl.

In another embodiment A is —CH$_2$—O—(CH$_2$)$_4$—, and D is t-butylphenyl.

In another embodiment A is —CH$_2$—O—CH$_2$—Ar—, wherein Ar is 2,5-interthienylene, and D is t-butylphenyl.

In another embodiment A is —CH$_2$—O—CH$_2$—Ar—, wherein Ar is 2,5-interfurylene, and D is t-butylphenyl.

In one embodiment A is —(CH$_2$)$_6$—, and D is (cyclohexylhydroxymethyl)phenyl.

In another embodiment A is cis —CH$_2$CH=CH—(CH$_2$)$_3$—, and D is (cyclohexylhydroxymethyl)phenyl.

In another embodiment A is —CH$_2$C≡C—(CH$_2$)$_3$—, and D is (cyclohexylhydroxymethyl)phenyl.

In another embodiment A is —S(CH$_2$)$_3$S(CH$_2$)$_2$—, and D is (cyclohexylhydroxymethyl)phenyl.

In another embodiment A is —(CH$_2$)$_4$OCH$_2$—, and D is (cyclohexylhydroxymethyl)phenyl.

In another embodiment A is cis —CH$_2$CH=CH—CH$_2$OCH$_2$—, and D is (cyclohexylhydroxymethyl)phenyl.

In another embodiment A is —CH$_2$CH≡CH—CH$_2$OCH$_2$—, and D is (cyclohexylhydroxymethyl)phenyl.

In another embodiment A is —(CH$_2$)$_2$S(CH$_2$)$_3$—, and D is (cyclohexylhydroxymethyl)phenyl.

In another embodiment A is —CH$_2$-Ph-OCH$_2$—, wherein Ph is interphenylene, and D is (cyclohexylhydroxymethyl)phenyl.

In another embodiment A is —CH$_2$-mPh-OCH$_2$—, wherein mPh is m-interphenylene, and D is (cyclohexylhydroxymethyl)phenyl.

In another embodiment A is —CH$_2$—O—(CH$_2$)$_4$—, and D is (cyclohexylhydroxymethyl)phenyl.

In another embodiment A is —CH$_2$—O—CH$_2$—Ar—, wherein Ar is 2,5-interthienylene, and D is (cyclohexylhydroxymethyl)phenyl.

In another embodiment A is —CH$_2$—O—CH$_2$—Ar—, wherein Ar is 2,5-interfurylene, and D is (cyclohexylhydroxymethyl)phenyl.

In one embodiment A is —(CH$_2$)$_6$—, and D is (cyclohexylmethyl)phenyl.

In another embodiment A is cis —CH$_2$CH=CH—(CH$_2$)$_3$—, and D is (cyclohexylmethyl)phenyl.

In another embodiment A is —CH$_2$C≡C—(CH$_2$)$_3$—, and D is (cyclohexylmethyl)phenyl.

In another embodiment A is —S(CH$_2$)$_3$S(CH$_2$)$_2$—, and D is (cyclohexylmethyl)phenyl.

In another embodiment A is —(CH$_2$)$_4$OCH$_2$—, and D is (cyclohexylmethyl)phenyl.

In another embodiment A is cis —CH$_2$CH=CH—CH$_2$OCH$_2$—, and D is (cyclohexylmethyl)phenyl.

In another embodiment A is —CH$_2$CH≡CH—CH$_2$OCH$_2$—, and D is (cyclohexylmethyl)phenyl.

In another embodiment A is —(CH$_2$)$_2$S(CH$_2$)$_3$—, and D is (cyclohexylmethyl)phenyl.

In another embodiment A is —CH$_2$-Ph-OCH$_2$—, wherein Ph is interphenylene, and D is (cyclohexylmethyl)phenyl.

In another embodiment A is —CH$_2$-mPh-OCH$_2$—, wherein mPh is m-interphenylene, and D is (cyclohexylmethyl)phenyl.

In another embodiment A is —CH$_2$—O—(CH$_2$)$_4$—, and D is (cyclohexylmethyl)phenyl.

In another embodiment A is —CH$_2$—O—CH$_2$—Ar—, wherein Ar is 2,5-interthienylene, and D is (cyclohexylmethyl)phenyl.

In another embodiment A is —CH$_2$—O—CH$_2$—Ar—, wherein Ar is 2,5-interfurylene, and D is (cyclohexylmethyl)phenyl.

In one embodiment A is —(CH$_2$)$_6$—, and D is indanyl.

In another embodiment A is cis—CH$_2$CH=CH—(CH$_2$)$_3$—, and D is indanyl.

In another embodiment A is —CH$_2$C≡C—(CH$_2$)$_3$—, and D is indanyl.

In another embodiment A is —S(CH$_2$)$_3$S(CH$_2$)$_2$—, and D is indanyl.

In another embodiment A is —(CH$_2$)$_4$OCH$_2$—, and D is indanyl.

In another embodiment A is cis—CH$_2$CH=CH—CH$_2$OCH$_2$—, and D is indanyl.

In another embodiment A is —CH$_2$CH≡CH—CH$_2$OCH$_2$—, and D is indanyl.

In another embodiment A is —(CH$_2$)$_2$S(CH$_2$)$_3$—, and D is indanyl.

In another embodiment A is —CH$_2$-Ph-OCH$_2$—, wherein Ph is interphenylene, and D is indanyl.

In another embodiment A is —CH$_2$-mPh-OCH$_2$—, wherein mPh is m-interphenylene, and D is indanyl.

In another embodiment A is —CH$_2$—O—(CH$_2$)$_4$—, and D is indanyl.

In another embodiment A is —CH$_2$—O—CH$_2$—Ar—, wherein Ar is 2,5-interthienylene, and D is indanyl.

In another embodiment A is —CH$_2$—O—CH$_2$—Ar—, wherein Ar is 2,5-interfurylene, and D is indanyl.

In one embodiment A is —(CH$_2$)$_6$—, and D is indanolyl.

In another embodiment A is cis—CH$_2$CH=CH—(CH$_2$)$_3$—, and D is indanolyl.

In another embodiment A is —CH$_2$C≡C—(CH$_2$)$_3$—, and D is indanolyl.

In another embodiment A is —S(CH$_2$)$_3$S(CH$_2$)$_2$—, and D is indanolyl.

In another embodiment A is —(CH$_2$)$_4$OCH$_2$—, and D is indanolyl.

In another embodiment A is cis —CH$_2$CH=CH—CH$_2$OCH$_2$—, and D is indanolyl.

In another embodiment A is —CH$_2$CH≡CH—CH$_2$OCH$_2$—, and D is indanolyl.

In another embodiment A is —(CH$_2$)$_2$S(CH$_2$)$_3$—, and D is indanolyl.

In another embodiment A is —CH$_2$-Ph-OCH$_2$—, wherein Ph is interphenylene, and D is indanolyl.

In another embodiment A is —CH$_2$-mPh-OCH$_2$—, wherein mPh is m-interphenylene, and D is indanolyl.

In another embodiment A is —CH$_2$—O—(CH$_2$)$_4$—, and D is indanolyl.

In another embodiment A is —CH$_2$—O—CH$_2$—Ar—, wherein Ar is 2,5-interthienylene, and D is indanolyl.

In another embodiment A is —CH$_2$—O—CH$_2$—Ar—, wherein Ar is 2,5-interfurylene, and D is indanolyl.

In one embodiment A is —(CH$_2$)$_6$—, and D is indanonyl.

In another embodiment A is cis—CH$_2$CH=CH—(CH$_2$)$_3$—, and D is indanonyl.

In another embodiment A is —CH$_2$C≡C—(CH$_2$)$_3$—, and D is indanonyl.

In another embodiment A is —S(CH$_2$)$_3$S(CH$_2$)$_2$—, and D is indanonyl.

In another embodiment A is —(CH$_2$)$_4$OCH$_2$—, and D is indanonyl.

In another embodiment A is cis —CH$_2$CH=CH—CH$_2$OCH$_2$—, and D is indanonyl.

In another embodiment A is —CH$_2$CH≡CH—CH$_2$OCH$_2$—, and D is indanonyl.

In another embodiment A is —(CH$_2$)$_2$S(CH$_2$)$_3$—, and D is indanonyl.

In another embodiment A is —CH$_2$-Ph-OCH$_2$—, wherein Ph is interphenylene, and D is indanonyl.

In another embodiment A is —CH$_2$-mPh-OCH$_2$—, wherein mPh is m-interphenylene, and D is indanonyl.

In another embodiment A is —CH$_2$—O—(CH$_2$)$_4$—, and D is indanonyl.

In another embodiment A is —CH$_2$—O—CH$_2$—Ar—, wherein Ar is 2,5-interthienylene, and D is indanonyl.

In another embodiment A is —CH$_2$—O—CH$_2$—Ar—, wherein Ar is 2,5-interfurylene, and D is indanonyl.

In one embodiment A is —(CH$_2$)$_6$—, and D is (1-hydroxycyclobutyl)phenyl.

In another embodiment A is cis —CH$_2$CH=CH—(CH$_2$)$_3$—, and D is (1-hydroxycyclobutyl)phenyl.

In another embodiment A is —CH$_2$C≡C—(CH$_2$)$_3$—, and D is (1-hydroxycyclobutyl)phenyl.

In another embodiment A is —S(CH$_2$)$_3$S(CH$_2$)$_2$—, and D is (1-hydroxycyclobutyl)phenyl.

In another embodiment A is —(CH$_2$)$_4$OCH$_2$—, and D is (1-hydroxycyclobutyl)phenyl.

In another embodiment A is cis —CH$_2$CH=CH—CH$_2$OCH$_2$—, and D is (1-hydroxycyclobutyl)phenyl.

In another embodiment A is —CH$_2$CH≡CH—CH$_2$OCH$_2$—, and D is (1-hydroxycyclobutyl)phenyl.

In another embodiment A is —(CH$_2$)$_2$S(CH$_2$)$_3$—, and D is (1-hydroxycyclobutyl)phenyl.

In another embodiment A is —CH$_2$-Ph-OCH$_2$—, wherein Ph is interphenylene, and D is (1-hydroxycyclobutyl)phenyl.

In another embodiment A is —CH$_2$-mPh-OCH$_2$—, wherein mPh is m-interphenylene, and D is (1-hydroxycyclobutyl)phenyl.

In another embodiment A is —CH$_2$—O—(CH$_2$)$_4$—, and D is (1-hydroxycyclobutyl)phenyl.

In another embodiment A is —CH$_2$—O—CH$_2$—Ar—, wherein Ar is 2,5-interthienylene, and D is (1-hydroxycyclobutyl)phenyl.

In another embodiment A is —CH$_2$—O—CH$_2$—Ar—, wherein Ar is 2,5-interfurylene, and D is (1-hydroxycyclobutyl)phenyl.

In one embodiment A is —(CH$_2$)$_6$—, and D is (2-methyl-3-hydroxypropyl)phenyl.

In another embodiment A is cis —CH$_2$CH=CH—(CH$_2$)$_3$—, and D is (2-methyl-3-hydroxypropyl)phenyl.

In another embodiment A is —CH$_2$C≡C—(CH$_2$)$_3$—, and D is (2-methyl-3-hydroxypropyl)phenyl.

In another embodiment A is —S(CH$_2$)$_3$S(CH$_2$)$_2$—, and D is (2-methyl-3-hydroxypropyl)phenyl.

In another embodiment A is —(CH$_2$)$_4$OCH$_2$—, and D is (2-methyl-3-hydroxypropyl)phenyl.

In another embodiment A is cis —CH$_2$CH=CH—CH$_2$OCH$_2$—, and D is (2-methyl-3-hydroxypropyl)phenyl.

In another embodiment A is —CH$_2$CH≡CH—CH$_2$OCH$_2$—, and D is (2-methyl-3-hydroxypropyl)phenyl.

In another embodiment A is —(CH$_2$)$_2$S(CH$_2$)$_3$—, and D is (2-methyl-3-hydroxypropyl)phenyl.

In another embodiment A is —CH₂-Ph-OCH₂—, wherein Ph is interphenylene, and D is (2-methyl-3-hydroxypropyl)phenyl.

In another embodiment A is —CH₂-mPh-OCH₂—, wherein mPh is m-interphenylene, and D is (2-methyl-3-hydroxypropyl)phenyl.

In another embodiment A is —CH₂—O—(CH₂)₄—, and D is (2-methyl-3-hydroxypropyl)phenyl.

In another embodiment A is —CH₂—O—CH₂—Ar—, wherein Ar is 2,5-interthienylene, and D is (2-methyl-3-hydroxypropyl)phenyl.

In another embodiment A is —CH₂—O—CH₂—Ar—, wherein Ar is 2,5-interfurylene, and D is (2-methyl-3-hydroxypropyl)phenyl.

In one embodiment A is —(CH₂)₆—, and D is (1-hydroxy-2-phenylethyl)phenyl.

In another embodiment A is cis —CH₂CH=CH—(CH₂)₃—, and D is (1-hydroxy-2-phenylethyl)phenyl.

In another embodiment A is —CH₂C≡C—(CH₂)₃—, and D is (1-hydroxy-2-phenylethyl)phenyl.

In another embodiment A is —S(CH₂)₃S(CH₂)₂—, and D is (1-hydroxy-2-phenylethyl)phenyl.

In another embodiment A is —(CH₂)₄OCH₂—, and D is (1-hydroxy-2-phenylethyl)phenyl.

In another embodiment A is cis —CH₂CH=CH—CH₂OCH₂—, and D is (1-hydroxy-2-phenylethyl)phenyl.

In another embodiment A is —CH₂CH═CH—CH₂OCH₂—, and D is (1-hydroxy-2-phenylethyl)phenyl.

In another embodiment A is —(CH₂)₂S(CH₂)₃—, and D is (1-hydroxy-2-phenylethyl)phenyl.

In another embodiment A is —CH₂-Ph-OCH₂—, wherein Ph is interphenylene, and D is (1-hydroxy-2-phenylethyl)phenyl.

In another embodiment A is —CH₂-mPh-OCH₂—, wherein mPh is m-interphenylene, and D is (1-hydroxy-2-phenylethyl)phenyl.

In another embodiment A is —CH₂—O—(CH₂)₄—, and D is (1-hydroxy-2-phenylethyl)phenyl.

In another embodiment A is —CH₂-O—CH₂—Ar—, wherein Ar is 2,5-interthienylene, and D is (1-hydroxy-2-phenylethyl)phenyl.

In another embodiment A is —CH₂-O—CH₂—Ar—, wherein Ar is 2,5-interfurylene, and D is (1-hydroxy-2-phenylethyl)phenyl.

One embodiment comprises

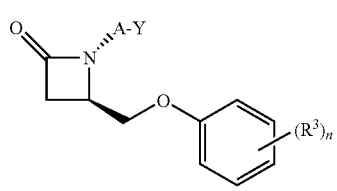

or a pharmaceutically acceptable salt or a prodrug or a metabolite thereof;

$R^3$ is independently methyl, ethyl, isopropyl, fluoro, chloro, bromo, methoxy, ethoxy, isopropoxy, $NH_2$, OH, CN, $NO_2$, or $CF_3$; and n is 0, 1, 2, or 3.

Another embodiment comprises

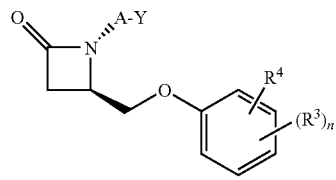

or a pharmaceutically acceptable salt or a prodrug or a metabolite thereof;

wherein A and Y are as described herein;

$R^3$ is independently methyl, ethyl, isopropyl, fluoro, chloro, bromo, methoxy, ethoxy, isopropoxy, $NH_2$, OH, CN, $NO_2$, or $CF_3$;

$R^4$ is hydroxyhydrocarbyl having from 1 to 10 carbon atoms; and n is 0, 1, 2, or 3.

Other embodiments comprise compounds according to the structures below, or pharmaceutically acceptable salts or prodrugs thereof. In these embodiments A is as described herein; and Y, $R^3$ and n are as described herein.

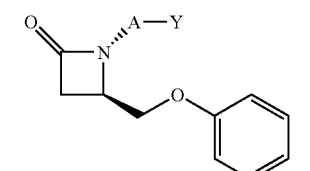

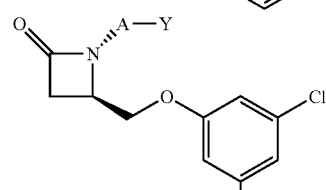

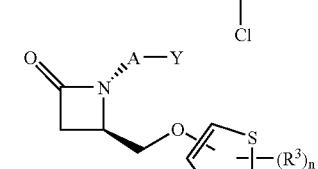

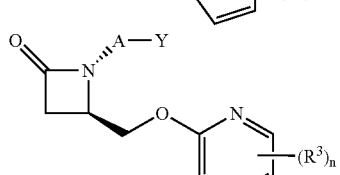

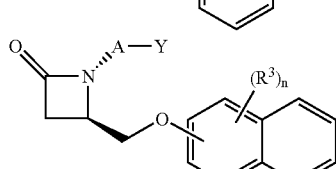

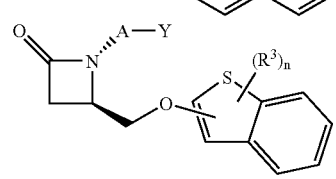

Another embodiment comprises

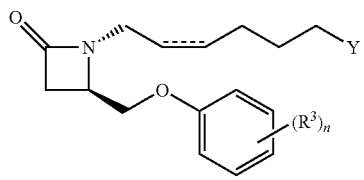

or a pharmaceutically acceptable salt or a prodrug or a metabolite thereof;
wherein a dashed line indicates the presence or absence of a covalent bond A is as described herein;
$R^3$ is independently methyl, ethyl, isopropyl, fluoro, chloro, bromo, methoxy, ethoxy, isopropoxy, $NH_2$, OH, CN, $NO_2$, or $CF_3$; and
n is 0, 2, or 3.

Other embodiments comprise compounds according to the structures below, or pharmaceutically acceptable salts or prodrugs thereof. In these embodiments Y, $R^3$ and n are as described herein.

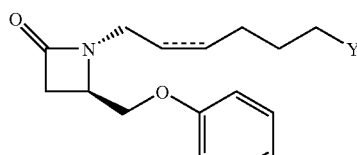

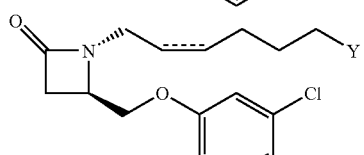

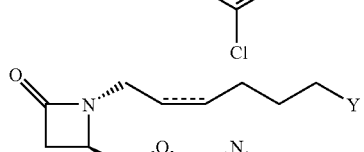

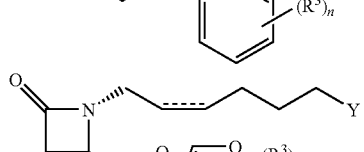

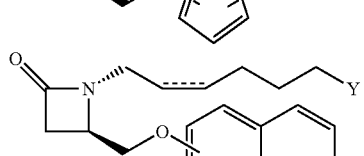

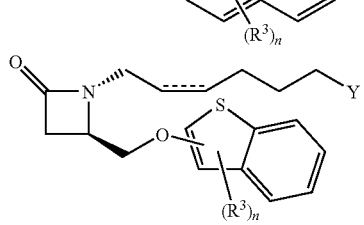

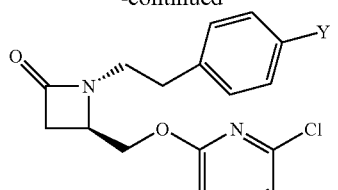

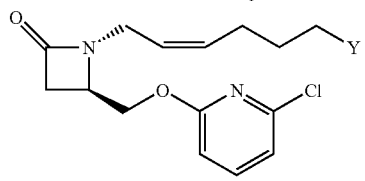

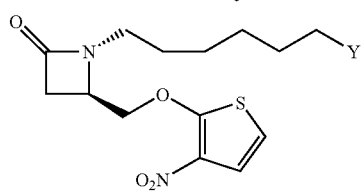

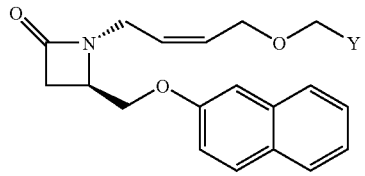

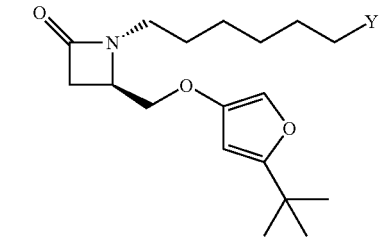

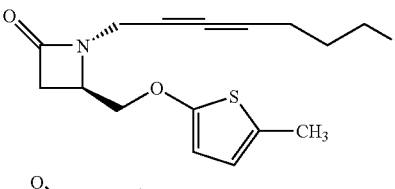

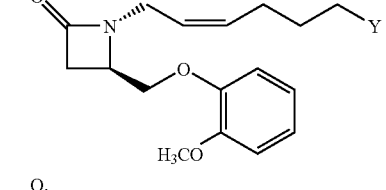

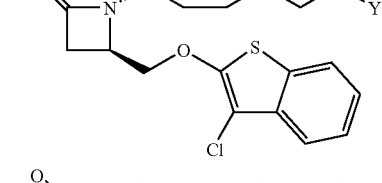

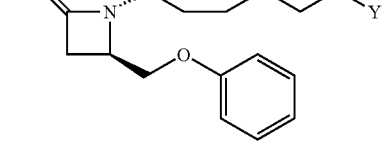

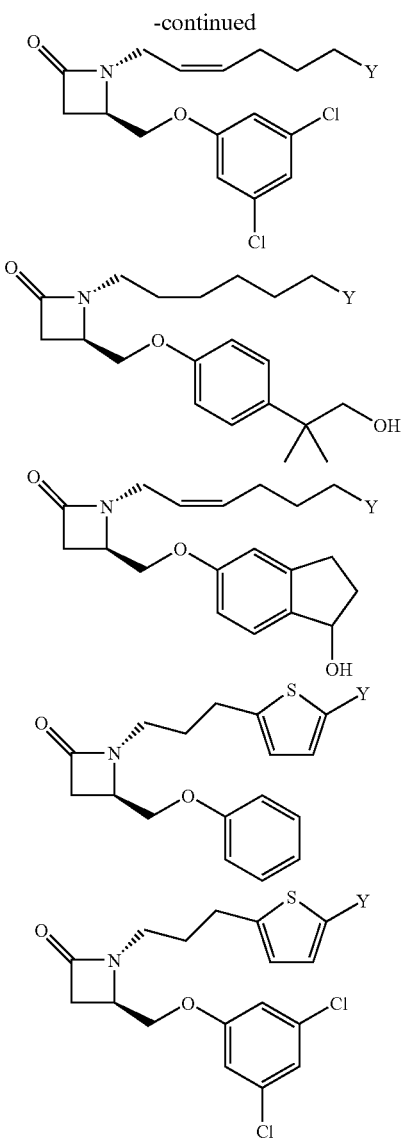

Another embodiment is a compound comprising a 4-(aryloxymethyl)azetidin-2-one or a 4-(heteroaryloxymethyl)azetidin-2-one, substituted at the beta lactam nitrogen with a prostaglandin a chain, wherein said compound is active at a prostaglandin EP2 receptor.

Aryloxymethyl is methyl having attached to an —OAr substituent, where Ar is aryl. Heteroaryloxymethyl is methyl attached to an —OHet substituent, where Het is heteroaryl. Aryloxy or heteroaryloxy is substituted or unsubstituted, i.e. the aryl or heteroaryl may be substituted or unsubstituted.

A prostaglandin a chain is any moiety which is the α-chain of any known prostaglandin, i.e. an analog for the numbered carbons 1-7 on the prostanoic acid structure shown above.

Pharmaceutically acceptable salts or prodrugs or metabolites of the above listed compounds are also contemplated.

The determination of whether a compound is active at a prostaglandin EP2 receptor is well within the ability of a person of ordinary skill in the art. While not intending to limit the scope of the invention in any way, one method of making such a determination is also provided in the examples herein.

The compounds of disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_2$ agonist, such as the ones listed previously.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, isobutyl, t-butyl, pentyl isomers, hexyl isomers, cyclopropyl, cyclobutyl, cyclopentyl, cyclohexyl, and combinations thereof having from 1-6 carbon atoms, etc.

A metabolite is broadly defined as a compound which is formed in vivo from the disclosed compound.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physologicla acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matricies for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs is contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including
non-selective adrenergic agonists such as epinephrine borate, epinephrine hydrochloride, and dipivefrin, and the like, or pharmaceutically acceptable salts or prodrugs thereof; and
α$_2$-selective adrenergic agonists such as apraclonidine, brimonidine, and the like, or pharmaceutically acceptable salts or prodrugs thereof;
Carbonic Anhydrase Inhibitors including acetazolamide, dichlorphenamide, methazolamide, brinzolamide, dorzolamide, and the like, or pharmaceutically acceptable salts or prodrugs thereof;
Cholinergic Agonists including
direct acting cholinergic agonists such as charbachol, pilocarpine hydrochloride, pilocarbine nitrate, pilocarpine, and the like, or pharmaceutically acceptable salts or prodrugs thereof;
chlolinesterase inhibitors such as demecarium, echothiophate, physostigmine, and the like, or pharmaceutically acceptable salts or prodrugs thereof;
Glutamate Antagonists such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;
Prostamides such as bimatoprost, or pharmaceutically acceptable salts or prodrugs thereof; and
Prostaglandins including travoprost, UFO-21, chloprostenol, fluprostenol, 13,14-dihydro-chloprostenol, latanoprost and the like.

The compounds disclosed herein can be selective prostaglandin EP$_2$ agonists, and are thus useful for the treatment of glaucoma, ocular hypertension, the other diseases or conditions disclosed herein.

One embodiment is a method comprising administering an effective amount of a compound to a mammal for the treatment or prevention of glaucoma or ocular hypertension, said compound comprising

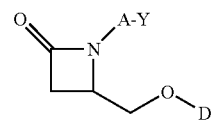

or a pharmaceutically acceptable salt or a prodrug or a metabolite thereof;
Y is

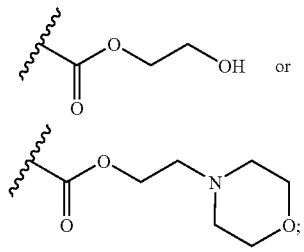

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and
D is aryl or heteroaryl.

Another embodiment is a method comprising administering an effective amount of a compound to a mammal for the treatment or prevention of glaucoma or ocular hypertension, said compound comprising

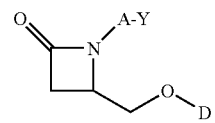

or a pharmaceutically acceptable salt or a prodrug or a metabolite thereof;
wherein A and Y are as defined above and D is phenyl.

Another embodiment is a method comprising administering an effective amount of a compound to a mammal for the treatment or prevention of glaucoma or ocular hypertension, said compound comprising

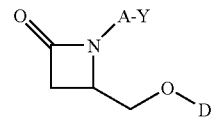

or a pharmaceutically acceptable salt or a prodrug or a metabolite thereof;

wherein A and Y are as defined above and D is chlorophenyl.

Another embodiment is a method comprising administering an effective amount of a compound to a mammal for the treatment or prevention of glaucoma or ocular hypertension, said compound comprising

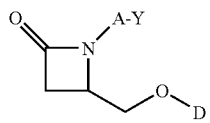

or a pharmaceutically acceptable salt or a prodrug or a metabolite thereof;

wherein A and Y are as defined above and D is 3,5-dichlorophenyl.

Another embodiment is a method comprising administering an effective amount of a compound to a mammal for the treatment or prevention of glaucoma or ocular hypertension, said compound comprising

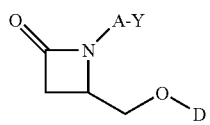

or a pharmaceutically acceptable salt or a prodrug or a metabolite thereof;

wherein A and Y are as defined above and D is unsubstituted phenyl.

Another embodiment is a method comprising administering an effective amount of a compound to a mammal for the treatment or prevention of glaucoma or ocular hypertension, said compound comprising

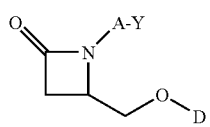

or a pharmaceutically acceptable salt or a prodrug or a metabolite thereof;

wherein A is —$(CH_2)_6$—, cis —$CH_2CH{=}CH$—$(CH_2)_3$—, or —$CH_2C{\equiv}C$—$(CH_2)_3$— and Y and D are as defined above.

Another embodiment is a method comprising administering an effective amount of a compound to a mammal for the treatment or prevention of glaucoma or ocular hypertension, said compound comprising

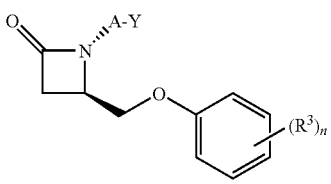

or a pharmaceutically acceptable salt or a prodrug or a metabolite thereof;

wherein A and Y are as defined above, $R^3$ is independently methyl, ethyl, isopropyl, fluoro, chloro, bromo, methoxy, ethoxy, isopropoxy, $NH_2$, OH, CN, $NO_2$, or $CF_3$; and n is 0, 1, 2, or 3.

Another embodiment is a method comprising administering an effective amount of a compound to a mammal for the treatment or prevention of glaucoma or ocular hypertension, said compound comprising

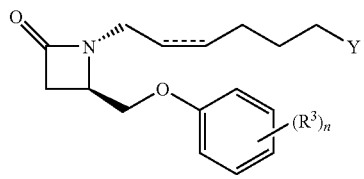

or a pharmaceutically acceptable salt or a prodrug or a metabolite thereof;

wherein a dashed line indicates the presence or absence of a covalent bond and $R^3$ and n are as defined above.

Another embodiment is a method comprising administering an effective amount of a compound to a mammal for the treatment or prevention of glaucoma or ocular hypertension, said compound comprising

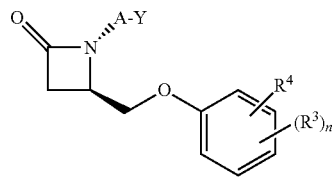

or a pharmaceutically acceptable salt or a prodrug or a metabolite thereof;

wherein A and Y are as defined above;

$R^3$ is independently methyl, ethyl, isopropyl, fluoro, chloro, bromo, methoxy, ethoxy, isopropoxy, $NH_2$, OH, CN, $NO_2$, or $CF_3$;

$R^4$ is hydroxyhydrocarbyl having from 1 to 10 carbon atoms; and n is 0, 1, 2, or 3.

Another embodiment is a method comprising administering an effective amount of a compound to a mammal for the treatment or prevention of glaucoma or ocular hypertension, said compound comprising a 4-(aryloxymethyl)azetidin-2-one or a 4-(heteroaryloxymethyl)azetidin-2-one, substituted at the beta lactam nitrogen with a prostaglandin a chain, wherein said compound is active at a prostaglandin $EP_2$ receptor.

One embodiment is a compound comprising

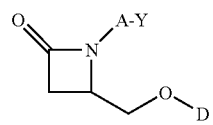

or a pharmaceutically acceptable salt or a prodrug or a metabolite thereof;

Y is

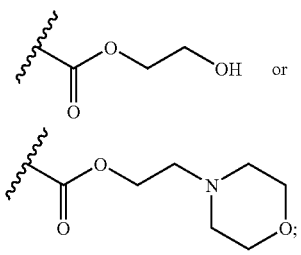

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is interarylene or heterointerarylene, the sum of m and o is from 1 to 4, and wherein one CH$_2$ may be substituted with S or O; and D is aryl or heteroaryl.

Another embodiment is a compound comprising

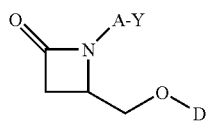

or a pharmaceutically acceptable salt or a prodrug or a metabolite thereof;

wherein A and Y are as defined above and D is phenyl.

Another embodiment is a compound comprising

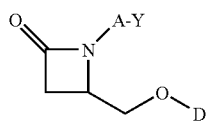

or a pharmaceutically acceptable salt or a prodrug or a metabolite thereof;

wherein A and Y are as defined above and D is chlorophenyl.

Another embodiment is a compound comprising

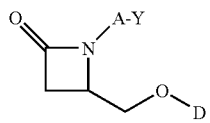

or a pharmaceutically acceptable salt or a prodrug or a metabolite thereof;

wherein A and Y are as defined above and D is 3,5-dichlorophenyl.

Another embodiment is a compound comprising

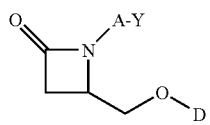

or a pharmaceutically acceptable salt or a prodrug or a metabolite thereof;

wherein A and Y are as defined above and D is unsubstituted phenyl.

Another embodiment is a compound comprising

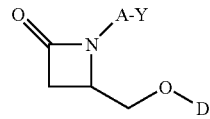

or a pharmaceutically acceptable salt or a prodrug or a metabolite thereof;

wherein A is —(CH$_2$)$_6$—, cis —CH$_2$CH=CH—(CH$_2$)$_3$—, or —CH$_2$C≡C—(CH$_2$)$_3$— and Y and D are as defined above.

Another embodiment is a compound comprising

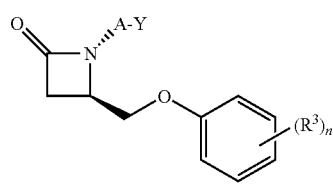

or a pharmaceutically acceptable salt or a prodrug or a metabolite thereof;

wherein A and Y are as defined above,

R$^3$ is independently methyl, ethyl, isopropyl, fluoro, chloro, bromo, methoxy, ethoxy, isopropoxy, NH$_2$, OH, CN, NO$_2$, or CF$_3$; and n is 0, 1, 2, or 3.

Another embodiment is a compound comprising

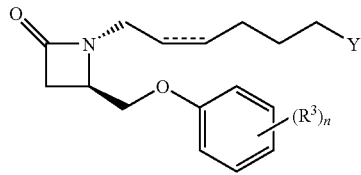

or a pharmaceutically acceptable salt or a prodrug or a metabolite thereof;

wherein a dashed line indicates the presence or absence of a covalent bond and R$^3$ and n are as defined above.

Another embodiment is a compound comprising

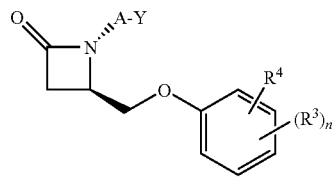

or a pharmaceutically acceptable salt or a prodrug or a metabolite thereof;

wherein A and Y are as defined above;

R$^3$ is independently methyl, ethyl, isopropyl, fluoro, chloro, bromo, methoxy, ethoxy, isopropoxy, NH$_2$, OH, CN, NO$_2$, or CF$_3$;

$R^4$ is hydroxyhydrocarbyl having from 1 to 10 carbon atoms; and n is 0, 1, 2, or 3.

Another embodiment is a compound comprising a 4-(aryloxymethyl)azetidin-2-one or a 4-(heteroaryloxymethyl)azetidin-2-one, substituted at the beta lactam nitrogen with a prostaglandin a chain, wherein said compound is active at a prostaglandin $EP_2$ receptor.

Another embodiment comprises administering an effective amount of a compound to a mammal for the treatment or prevention of glaucoma or ocular hypertension, said compound comprising any compound or class of compounds disclosed herein.

Another embodiment comprises administering an effective amount of a compound to a mammal for the treatment or prevention of inflammatory bowel disease, said compound comprising any compound or class of compounds disclosed herein.

Another embodiment comprises administering an effective amount of a compound to a mammal for the treatment of baldness, said compound comprising any compound or class of compounds disclosed herein.

Another embodiment comprises a liquid comprising a compound, wherein said liquid is ophthalmically acceptable, said compound comprising any compound or class of compounds disclosed herein.

Another embodiment comprises use of a compound in the manufacture of a medicament for the treatment of glaucoma or ocular hypertension in a mammal, said compound comprising any compound or class of compounds disclosed herein.

Another embodiment comprises use of a compound in the manufacture of a medicament for the treatment of baldness in a mammal, said compound comprising any compound or class of compounds disclosed herein.

Another embodiment comprises use of a compound in the manufacture of a medicament for the treatment of inflammatory bowel in a mammal, said compound comprising any compound or class of compounds disclosed herein.

SYNTHETIC PROCEDURES

While there are many methods of preparing the compounds disclosed herein, in one method the compound shown below may be prepared by the procedures described in Chemistry Letters, (2), 293-6; 1987 or U.S. Pat. No. 4,174,316, where the R, α-, or natural amino acid is substituted for the β or S amino acid used in the references.

Alternatively, (4R)-N-(tert-butyldimethylsilyl)azetidin-2-one-4-carboxylic acid (commercially available from Acros Chemical Company) could be converted in two steps (reduction [e.g. LiBH4, MeOH] and deprotection [e.g 1 N HCl, MeOH] to the compound shown below.

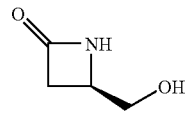

The α-chain may be added by adapting procedures known in the art, such as those described in U.S. Patent Application Publication No. 20030207925, U.S. Patent Application Publication No. 20030120079, and U.S. Pat. No. 6,747,054.

The w-chain may be constructed by procedures known in the art, such as those described in U.S. Patent Application Ser. No. 60/644,069 filed on Jan. 14, 2005.

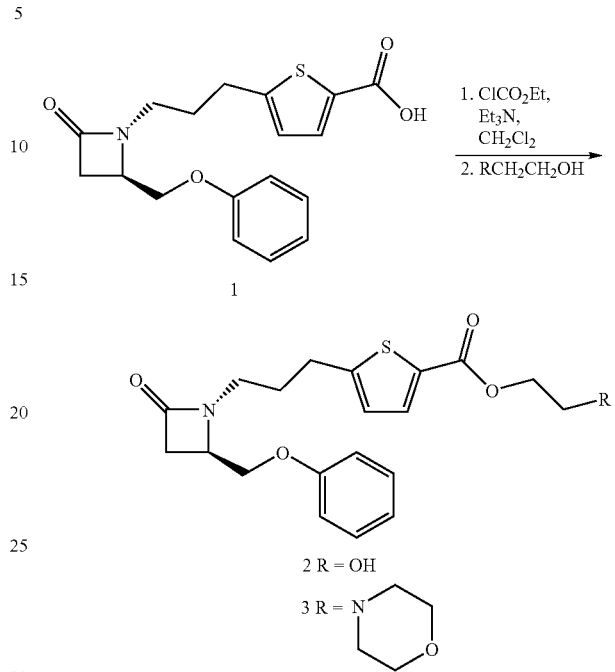

Compounds with Y as described herein can be synthesized according to the teachings of patent application Ser. No. 60/022,172. Scheme 1 demonstrates an exemplary method of synthesizing the α-chain as described herein.

IN VIVO EXAMPLES

Title compounds 2 and 3 from above are tested in vivo to measure its ability to reduce intraocular pressure. Compound 2 is tested in normotensive dogs. The intraocular pressure (IOP) decreases from baseline. This compound is also tested in laser-induced hypertensive monkeys, the IOP decreases from baseline.

Compound 3 is tested in normotensive dogs. The intraocular pressure (IOP) decreases from baseline. This compound is also tested in laser-induced hypertensive monkeys, the IOP decreases from baseline.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound of formula

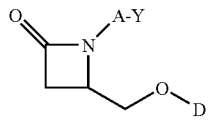

or a pharmaceutically acceptable salt or a prodrug thereof;
Y is

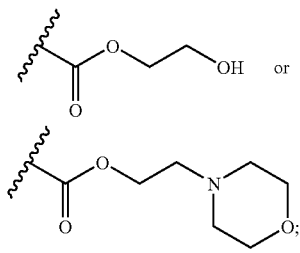

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_m$—Ar—(CH$_2$)$_o$—wherein Ar is interarylene or heterointerarylene, the sum of m and o is from 1 to 4, and wherein one CH$_2$ may be replaced with S or O; and
D is aryl or heteroaryl.

2. The compound of claim 1 of formula

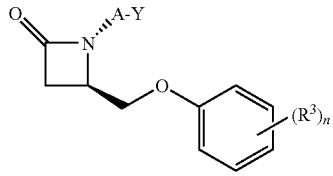

or a pharmaceutically acceptable salt or a prodrug thereof;
wherein R$^3$ is independently methyl, ethyl, isopropyl, fluoro, chloro, bromo, methoxy, ethoxy, isopropoxy, NH$_2$, OH, CN, NO$_2$, or CF$_3$; and
n is 0, 1, 2, or 3.

3. The compound of claim 1 of formula

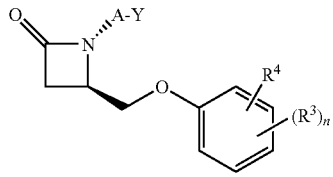

or a pharmaceutically acceptable salt or a prodrug thereof;

wherein R$^3$ is independently methyl, ethyl, isopropyl, fluoro, chloro, bromo, methoxy, ethoxy, isopropoxy, NH$_2$, OH, CN, NO$_2$, or CF$_3$;
R$^4$ is hydroxyhydrocarbyl having from 1 to 10 carbon atoms; and
n is 0, 1, 2, or 3.

4. The compound of claim 1 of formula

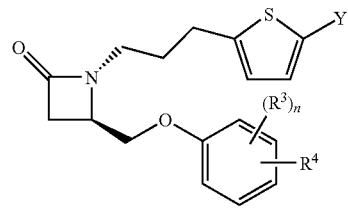

or a pharmaceutically acceptable salt or a prodrug thereof;
wherein R$^3$ is independently methyl, ethyl, isopropyl, fluoro, chloro, bromo, methoxy, ethoxy, isopropoxy, NH$_2$, OH, CN, NO$_2$, or CF$_3$;
R$^4$ is hydroxyhydrocarbyl having from 1 to 10 carbon atoms; and
n is 0, 1, 2, or 3.

5. The compound of claim 1 of formula

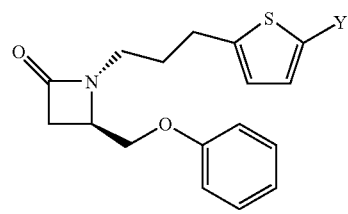

or a pharmaceutically acceptable salt or a prodrug thereof.

6. The compound of claim 1 comprising a formula

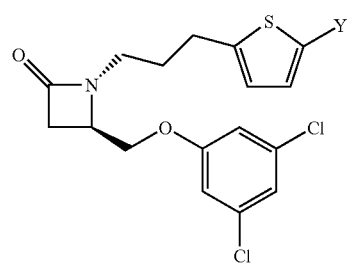

or a pharmaceutically acceptable salt or a prodrug thereof.

7. A method comprising administering a therapeutically effective amount of a compound according to claim 1 to a mammal for the treatment of baldness.

* * * * *